United States Patent [19]
Nielsen et al.

[11] Patent Number: 6,107,470
[45] Date of Patent: Aug. 22, 2000

[54] HISTIDINE-CONTAINING PEPTIDE NUCLEIC ACIDS

[76] Inventors: Peter E. Nielsen, Hjortevanget 509, DK 2980 Kokkedal; Ole Buchardt, deceased, late of Vaelose, by Dorte Buchardt, legal representative; Rolf H. Berg, Strandvanenget 6, 2960 Fungsted Kyst, all of Denmark; Michael Egholm, 34 Grove St., Wayland, Mass. 01778

[21] Appl. No.: 09/225,146

[22] Filed: Jan. 4, 1999

Related U.S. Application Data

[63] Continuation of application No. 09/169,705, Apr. 29, 1998.
[60] Provisional application No. 60/051,002, May 29, 1997.

[51] Int. Cl.[7] ............................ C07H 21/02; C07H 21/04; C07H 19/00; C12Q 1/68
[52] U.S. Cl. ............................ 536/23.1; 435/6; 536/22.1; 536/23.1; 536/24.31; 536/25.3
[58] Field of Search ................................ 435/6; 536/22.1, 536/23.1, 24.31, 25.3

[56] References Cited

FOREIGN PATENT DOCUMENTS 3329028  2/1985  Germany .

OTHER PUBLICATIONS

Dueholm, K.L. et al., "Peptide Nucleic Acid (PNA) with a Chiral Backbone Based on Alanine", *Biorg. Med. Chem. Letts.*, 1994, 4, 1077–1080.

Egholm, P.E. et al., "Sequence–Selective Recognition of DNA by Strand Displacement with a Thymine–Substituted Polyamide", *Science*, 1991, 254, 1497–1500.

Egholm, M. et al., "Peptide Nucleic Acids (PNA). Oligonucleotide Analogues with an Achiral Peptide Backbone", *J. Am. Chem Soc.*, 1992, 114, 1895–1897.

Egholm, M. et al., "Recognition of Guanine and Adenine inDNA by Cytosine and Thymine Containing Peptide Nucleic Acids (PNA)", *J. Am. Chem Soc.*, 1992, 114, 9677–9678.

Egholm, M. et al., "Peptide Nucleic Acids containing Adenine or Guanine recognise Thymine and Cytosine in Complementary DNA Sequences", *J. Chem. Soc. Chem. Comm.*, 1993, 800–801.

Egholm, M. et al., "PNA hybridizes to complementary oligonucleotides obeying the Watson–Crick hydrogen bonding rules", *Nature*, 1993, 365, 566–568.

Greene and Wuts, Protective Groups in Organic Synthesis, 2d Edition, John Wiley & Sons, New York, 1991.

Hanvey, J.C. et al., "Antisense and Antigene Properties of Peptide Nucleic Acids", *Science*, 1992, 258, 1481–1485.

Helene, C. et al., "Specific regulation of gene expression by antisense, sense, and antigene nucleic acids", *Biochimica et Biophysica Acta*, 1990, 1049, 99–125.

Hyrup, B. et al., "Modification of the Biniding Affinity of Peptide Nucleic Acids (PNA). PNA with extended Backbones Consisting of 2–Aminoethyl–β–alanine or 3–Aminopropylglycine Units", *J. Chem. Soc. Chem. Commun.*, 1993, 518–519.

Lagriffoul, P.H. et al., "The Synthesis, Co–Oligomerization and Hybridization of a Thymine–Thymine Heterodimer Containing PNA", *Bioor. Med. & Chem. Letts.*, 1994, 4, 1081–1082.

Nielsen, P.E. et al., "Sequence–Selective Recognition of DNA restriction enzyme cleavage by PNA", *Nucl. Acids Res.*, 1993, 21, 197–200.

Orum, H. et al., "Single base pair mutation analysis by PNA directed PCR clamping", *Nucl. Acids Res.*, 1993, 21(23), 5332–5336.

Uhlmann, E. et al., "Antisense Oligonucleotides: A New Therapeutic Principle", *Chem. Reviews*, 1990, 90, 544–584.

*Primary Examiner*—Jezia Riley
*Attorney, Agent, or Firm*—Woodcock Washburn Kurtz Mackiewicz & Norris LLP

[57] ABSTRACT

Peptide nucleic acids containing histidine moieties are provided. These compounds have applications including diagnostics, research and potential therapeutics.

6 Claims, 1 Drawing Sheet

HISTIDINE-CONTAINING PEPTIDE NUCLEIC ACIDS

This application is a continuation of Ser. No. 09/069,705 filed Apr. 29, 1998, and a provision of Ser. No. 60/051,002 filed May 29, 1997.

FIELD OF THE INVENTION

The present invention is directed to histidine-containing peptide nucleic acids and to synthetic intermediates employed in preparing such compounds.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with non isotopic labels, e.g. fluorescein, biotin, digoxigenin, alkaline phosphatase, or other reporter molecules.

Other modifications have been made to the ribose phosphate backbone to increase the nuclease stability of the resulting analog. These modifications include use of methyl phosphonates, phosphorothioates, phosphorodithioate linkages, and 2'-O-methyl ribose sugar units. Further modifications, include modifications made to modulate uptake and cellular distribution. Phosphorothioate oligonucleotides are presently being used as antisense agents in human clinical trials for various disease states including use as antiviral agents. With the success of these oligonucleotides for both diagnostic and therapeutic uses, there exists an ongoing demand for improved oligonucleotide analogs.

Oligonucleotides can interact with native DNA and RNA in several ways. One of these is duplex formation between an oligonucleotide and a single stranded nucleic acid. The other is triplex formation between an oligonucleotide and double stranded DNA to form a triplex structure.

In peptide nucleic acids, the deoxyribose backbone of oligonucleotides has been replaced with a backbone more akin to a peptide than a sugar. Each subunit, or monomer, has a naturally-occurring or non-naturally-occurring base attached to this backbone. One such backbone is constructed of repeating units of N-(2-aminoethyl)glycine linked through amide bonds. Because of the radical deviation from the deoxyribose backbone, these compounds were named peptide nucleic acids (PNAs).

PNAs bind both DNA and RNA to form PNA/DNA or PNA/RNA duplexes. The resulting PNA/DNA or PNA/RNA duplexes are bound with greater affinity than corresponding DNA/DNA or DNA/RNA duplexes as indicated by melt temperatures. This high thermal stability might be attributed to the lack of charge repulsion due to the neutral backbone in PNA. The neutral backbone of the PNA also results in the melt temperatures of PNA/DNA(RNA) duplex being practically independent of the salt concentration. Thus the PNA/DNA duplex interaction offers a further advantage over DNA/DNA duplex interactions which are highly dependent on ionic strength. Homopyrimidine PNAs have been shown to bind complementary DNA or RNA forming (PNA)2/DNA (RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

In addition to increased affinity, PNAs have also been shown to bind to DNA with increased specificity. When a PNA/DNA duplex mismatch is melted relative to the DNA/DNA duplex there is seen an 8 to 20° C. drop in the melt temperature (Tm). This magnitude of a drop in Tm is not seen with the corresponding DNA/DNA duplex with a mismatch present.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

PNAs bind to both single stranded DNA and double stranded DNA. As noted above, in binding to double stranded DNA it has been observed that two strands of PNA can bind to the DNA. While PNA/DNA duplexes are stable in the antiparallel configuration, it was previously believed that the parallel orientation is preferred for $(PNA)_2$/DNA.

The binding of two single stranded pyrimidine PNAs to a double stranded DNA has been shown to take place via strand displacement, rather than conventional triple helix formation as observed with triplexing oligonucleotides. When a PNA strand invades double stranded DNA, one strand of the DNA is displaced and forms a loop on the side of the $PNA_2$/DNA complex area. The other strand of the DNA is locked up in the $(PNA)_2$/DNA triplex structure. The loop area (alternately referenced as a D loop) being single stranded, is susceptible to cleavage by enzymes that can cleave single stranded DNA.

A further advantage of PNAs as compared to oligonucleotides is that their polyamide backbone (having appropriate nucleobases or other side chain groups attached thereto) is not recognized by either nucleases or proteases and are not cleaved. As a result PNAs are resistant to degradation by enzymes unlike nucleic acids and peptides.

These properties of PNAs make them useful in several areas. Since PNAs have stronger binding and greater specificity than oligonucleotides, they are used as probes in cloning, blotting procedures, and in applications such as fluorescence in situ hybridization (FISH). Homopyrimidine PNAs are used for strand displacement in homopurine targets. The restriction sites that overlap with or are adjacent to the D-loop are not cleaved by restriction enzymes. Also, the local triplex inhibits gene transcription. Thus in binding of PNAs to specific restriction sites within a DNA fragment, cleavage at those sites can be inhibited. Advantage can be taken of this in cloning and subcloning procedures. Labeled PNAs are also used to directly map DNA molecules. In effecting this, PNA molecules having a fluorescent label are hybridized to complementary sequences in duplex DNA using strand invasion.

PNAs have further been used to detect point mutations in PCR-based assays (PCR clamping). PCR clamping uses PNA to detect point mutations in a PCR-based assay, e.g., the distinction between a common wild type allele and a mutant allele, in a segment of DNA under investigation. A PNA oligomer complementary to the wild type sequence is synthesized. The PCR reaction mixture contains this PNA and two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, one can determine the presence and exact identity of a mutant.

Considerable research is being directed to the application of oligonucleotides and oligonucleotide analogs that bind complementary DNA and RNA strands for use as diagnostics, research reagents and potential therapeutics. PCT/EP/01219 describes novel peptide nucleic acid (PNA) compounds which bind complementary DNA and RNA more tightly than the corresponding DNA. Because of these binding properties as well as their stability, such PNA compounds find many uses in diagnostics and research reagents uses associated with both DNA and RNA. With complementary DNA and RNA they can form double-stranded, helical structures mimicking double-stranded DNA, and they are capable of being derivatized to bear pendant groups to further enhance or modulate their binding, cellular uptake, or other activity.

Thus, such oligomers and compositions comprising them are greatly desired.

SUMMARY OF THE INVENTION

One aspect of the present invention provides compounds of formula (I):

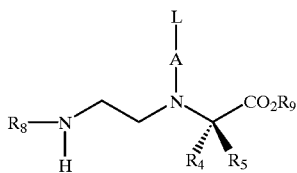

(I)

wherein:

$R_8$ is H or an amine protecting group;

$R_9$ is H, alkyl having from 1 to about 12 carbon atoms, or alkenyl having from 2 to about 12 carbon atoms;

one of $R_4$ and $R_5$ is H and the other of $R_4$ and $R_5$ is a moiety of formula (II)

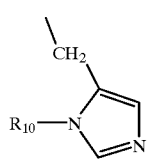

(II)

wherein $R_{10}$ is an amine protecting group;

L is selected from the group consisting of hydrogen, hydroxy, $(C_1-C_4)$alkanoyl, naturally occurring nucleobases, non-naturally occurring nucleobases, aromatic moieties, DNA intercalators, nucleobase-binding groups, and heterocyclic moieties, reporter ligands, wherein amino groups are, optionally, protected by amino protecting groups;

A is a group of formula (IIa)–(IId):

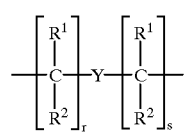

(IIA)

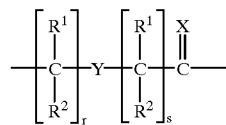

(IIb)

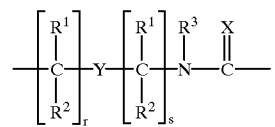

(IIc)

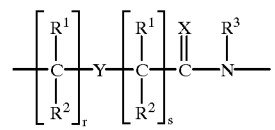

(IId)

where:

X is O, S, Se, $NR^3$, $CH_2$ or $C(CH_3)_2$;

Y is a single bond, O, S or $NR^4$ where $R^4$ is as described above;

each r and s is zero or an integer from 1 to 5;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and $R^3$ is selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino.

BRIEF DESCRIPTION OF THE FIGURES

The numerous objects and advantages of the present invention can be better understood by those skilled in the art by reference to the accompanying FIG. 1, which shows a representative synthetic scheme for compounds having formula (I).

DETAILED DESCRIPTION OF THE INVENTION

Figure 1:
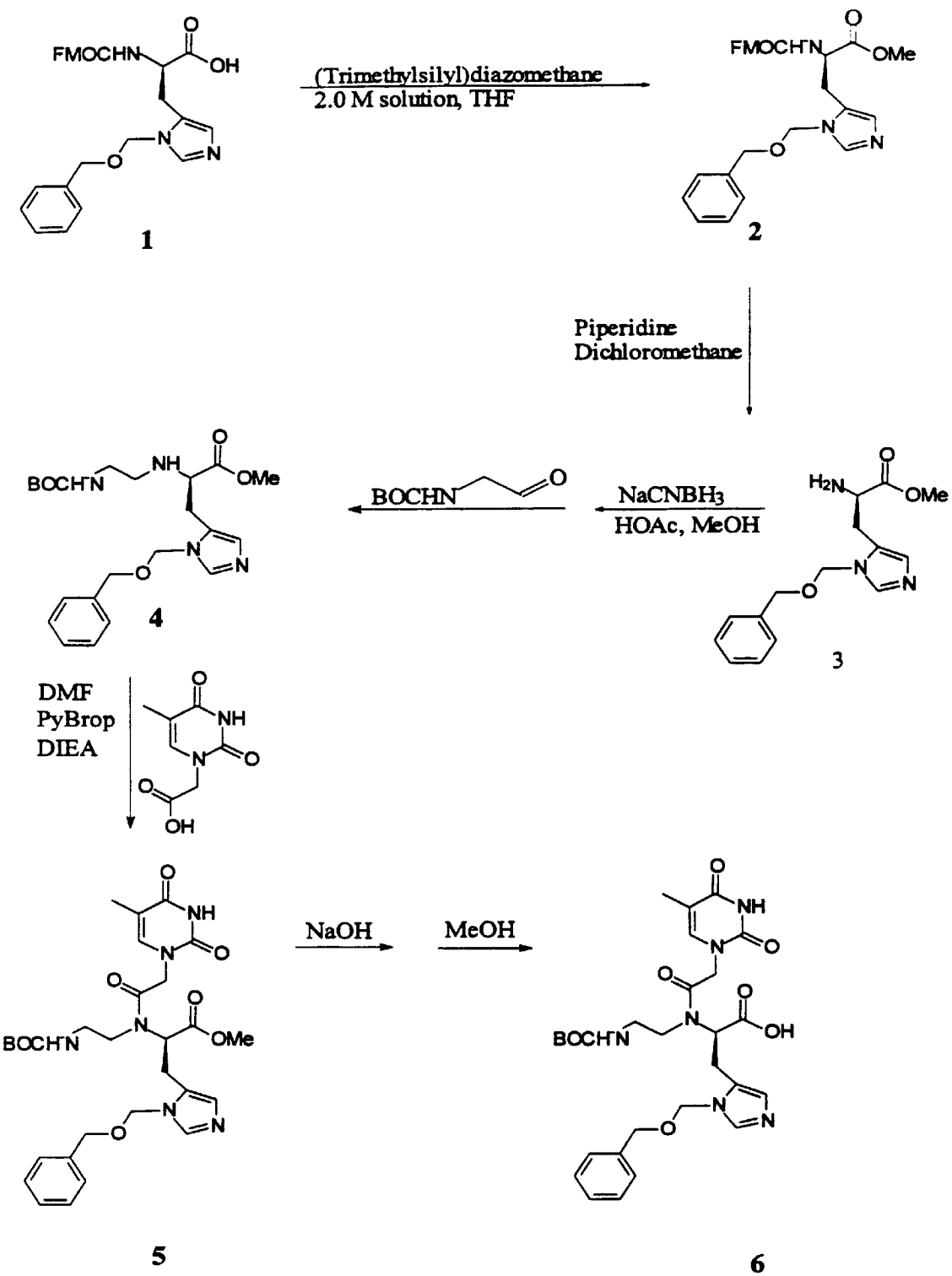

Specific sequence recognition of DNA or RNA is of increasing importance for the development of biological probes and new reagents for use in research (Uhlmann, E., Peyman, A., Chem. Rev., 1990, 90, 544, and Helene, C., Toulme, J. J., Biochim. Biophys. Acta., 1990, 1049, 99). Peptide nucleic acids (PNA), achiral analogs of DNA in which the nucleobases or nucleobase analogs are attached to a (2-aminoethyl)-glycine backbone through a methylene carbonyl linker, have properties making them well suited for use as biological probes and other applications. PNAs have shown strong binding affinity and specificity to complementary DNA, sequence specific inhibition of DNA restriction enzyme cleavage and site specific in vitro inhibition of translation (Egholm, M., et.al., Chem. Soc., Chem. Commun., 1993, 800; Egholm, M., et.al., Nature, 1993, 365, 566; Nielsen, M., et.al. Nucl. Acids Res., 1993, 21, 197; and Hanvey, J. C., et.al., Science, 1992, 258, 1481). Modifications of PNA include extended backbones (Hyrup, B., et.al. Chem. Soc., Chem. Commun., 1993, 518), extended linkers between the backbone and the nucleobase, reversal of the amido bond (Lagriffoul, P. H., et.al., Biomed. Chem. Lett., 1994, 4, 1081), and the use of a chiral backbone based on alanine (Dueholm, K. L, et.al., BioMed. Chem. Lett., 1994, 4, 1077).

The present invention is directed to PNAs which bear a histidine-containing moiety. Preferred compounds are those having formula (I):

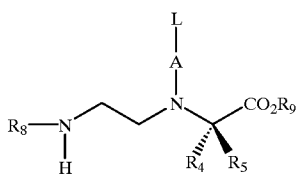
(I)

wherein $R_8$ is H or an amine protecting group;

$R_9$ is H, alkyl having from 1 to about 12 carbon atoms, or alkenyl having from 2 to about 12 carbon atoms, preferably an allyl group;

one of $R_4$ and $R_5$ is H and the other of $R_4$ and $R_5$ is a moiety of formula (II)

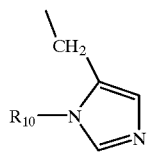
(II)

wherein $R_{10}$ is an amine protecting group;

L is selected from the group consisting of hydrogen, hydroxy, $(C_1-C_4)$alkanoyl, naturally occurring nucleobases, non-naturally occurring nucleobases, aromatic moieties, DNA intercalators, nucleobase-binding groups, and heterocyclic moieties, reporter ligands, wherein amino groups are, optionally, protected by amino protecting groups;

A is a group of formula (IIa)–(IId):

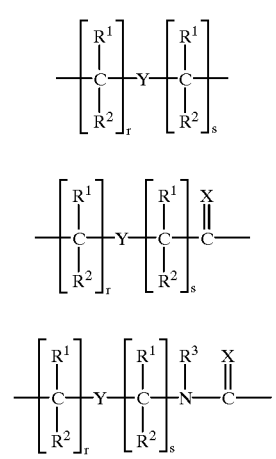

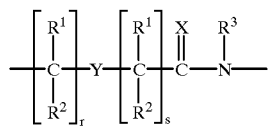
(IId)

where:

X is O, S, Se, $NR^3$, $CH_2$ or $C(CH_3)_2$;

Y is a single bond, O, S or $NR^4$ where $R^4$ is as described above;

each r and s is zero or an integer from 1 to 5;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and $R^3$ is selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino.

While not wishing to be bound by any particular theory, such compounds are believed to have enhanced uptake properties. It is known in the art that the introduction of positive charges on the backbone can increase cellular uptake. The histidine moiety is capable of a partial positive charge at physiological pH.

Alkyl groups according to the invention include but are not limited to straight chain, branched chain, and cyclic hydrocarbons such as methyl, ethyl, propyl, pentyl, isopropyl, 2-butyl, isobutyl, 2-methylbutyl, and isopentyl moieties having 1 to about 12 carbon atoms, preferably 1 to about 7 carbon atoms.

Aryl groups according to the invention are aromatic groups including, for example, benzyl, imidazolyl, naphthyl, phenyl, pyridyl, pyrimidinyl, and xylyl groups and substituted derivatives thereof, particularly those substituted with alkyl, alkoxy, amino, and nitro groups. Preferred aryl groups have 6 to about 14 carbon atoms.

The term amino acid as used herein is intended to include all naturally-occurring and synthetic amino acids known in the art. In general, amino acids have structure $H_2N-CH(R_C)-C(O)OH$ where $R_C$ is the amino acid side chain. Representative, naturally-occurring side chains are shown in Table 1.

TABLE 1

| | |
|---|---|
| $CH_3-$ | $CH_3-CH_2-S-CH_2-CH_2-$ |
| $HO-CH_2-$ | $HO-CH_2-CH_2-$ |
| $C_6H_5-CH_2-$ | $CH_3-CH_2(OH)-$ |

TABLE 1-continued

| | |
|---|---|
| HO—C₆H₅—CH₂— | HO₂C—CH₂—NH₂C(O)—CH₂— |
| 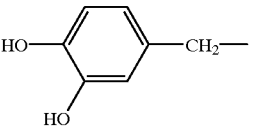 | 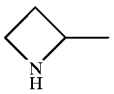 |
| 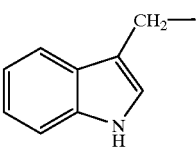 | HCO₂—CH₂—CH₂—<br>NH₂C(O)—CH₂—CH₂—<br>(CH₃)₂—CH—<br>(CH₃)₂—CH—CH₂—<br>CH₃—CH₂—CH₂— |
| 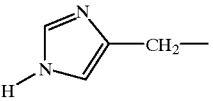 | H₂N—CH₂—CH₂—CH₂—<br>H₂N—C(NH)—NH—CH₂—CH₂—CH₂—<br>H₂N—C(O)—NH—CH₂—CH₂—CH₂—<br>CH₃—CH₂—CH(CH₃)— |
| HS—CH₂—<br>HO₂C—CH(NH₂)—CH₂—S—S—CH₂—<br>CH₃—CH₂—<br>CH₃—S—CH₂—CH₂— | CH₃—CH₂—CH₂—CH₂—<br>H₂N—CH₂—CH₂—CH₂—CH₂— |

Preferred side chains include those that exhibit polarity such as those having primary or secondary amines. A more preferred list includes HO—CH₂—, HO—C₆H₅—CH₂—, HO₂C—CH(NH₂)—CH₂—S—S—CH₂—, HO—CH₂—CH₂—, HCO₂—CH₂—CH₂—, H₂N—C(NH)—NH—CH₂—CH₂—CH₂—, H₂N—C(O)—NH—CH₂—CH₂—CH₂—, H₂N—CH₂—CH₂—CH₂—CH₂— and p-HO-m-HO—C₆H₄—CH₂—.

Nucleotide bases according to the invention include heterocyclic bases, including those which occur naturally in DNA and RNA, and modified bases. Modified bases are those in which the purine or pyrimidine ring is altered. Naturally occurring bases include adenine, guanine, hypoxanthine, xanthine, uracil, cytosine, and thymine. Exemplary modified bases include 6-methylaminopurine, 7-methylguanine, and 5-methylcytosine.

As indicated in FIG. 1, compounds of formula (IV) may be prepared by incorporating an amino acid protecting group into compounds of formula (V).

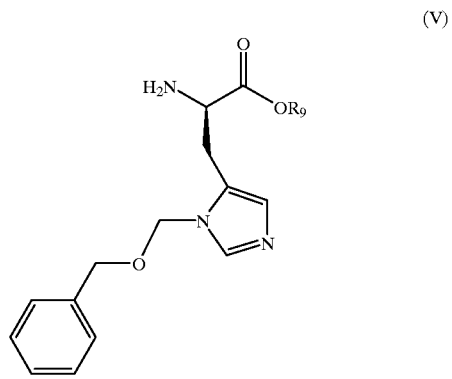

(V)

Protecting groups are known per se as chemical functional groups that can be selectively appended to and removed from functionality, such as amine, carboxyl, or hydroxyl groups, which present in a chemical compound, thus rendering such functionality inert to chemical reaction conditions to which the compound is exposed. See, e.g., Greene and Wuts, Protective Groups in Organic Synthesis, 2d edition, John Wiley & Sons, New York, 1991. Representative carboxyl protecting groups include lower (i.e., $C_1$–$C_7$) alkyl esters and benzyl esters. Preferred carboxyl protecting groups are those that are stable to moderately strong acid but can be removed with strongly acidic conditions.

Compounds having formula (IV) preferably are prepared by appending amine protecting groups directly to amino acids having formula (V). Suitable protecting groups in this regard include the allyloxycarbonyl (Alloc), benzyloxycarbonyl (CBz) and chlorobenzyloxycarbonyl groups. Some preferred amine protecting groups include t-butyloxycarbonyl (Boc), t-butyloxymethyl, fluorenylmethoxycarbonyl (Fmoc), 2,4-dinitrophenyl and isonicotinyloxycarbonyl (i-Noc) groups. Preferred amine protecting groups for direct attachment to amino acids are those that are stable to acidic conditions but can be removed under basic conditions.

Compounds of formula (V) can be readily obtained by alkylation of the corresponding amino acid, according to methods known to those skilled in the art. For example, compounds wherein $R_2$ is methyl may be prepared by methylation, using known methylating agents such as (trimethysilyl)diazomethane. Other methods include alkylation with diazomethane or preparation of the sodium salt of the carboxyl group followed by treatment with methyl iodide.

PNAs of the present invention are useful as research reagents and as diagnostic tools. PNAs have been used in studies to discriminate between fully complementary and single base mismatch targets (Orum, H., et.al., *Nucleic Acids Research*, 1993, 21, 5332–5336). The method utilizes the properties of PNA e.g. higher thermal stability, greater specificity when bound to complementary nucleic acid sequences than the corresponding deoxyribooligonucleotides and that PNAs are not recognized by DNA polymerase as primers. A PNA/DNA complex can effectively block the formation of a PCR product when the PNA is targeted against the PCR primer site. This method is effective in blocking target sequences when two target sequences in the same assay differ by only one base pair. Compounds of the present invention having greater specificity than normal PNA are well suited for use in diagnostic assays of this type.

The following examples are merely illustrative of the present invention and should not be considered limiting of the scope of the invention in any way. These examples and equivalents thereof will become more apparent to those skilled in the art in light of the present disclosure and the accompanying claims. The disclosures of each patent, patent application, and publication cited or described in this document are hereby incorporated herein by reference in their entirety. In the following examples, all numbers within parentheses refer to FIG. 1.

EXAMPLE 1

Nα-Fmoc-Π-benzyloxymethyl-L-histidine methyl ester (2)

To Nα-Fmoc-Π-benzyloxymethyl-L-histidine (Sigma Chemical Company, 9.0 gm, 18.1 mmol) in DMF (150 mL) was added (trimethylsilyl)diazomethane (20 mL, 40 mmol/2.0 M/THF). The mixture was stirred under an atmosphere of nitrogen for about 12 hours. The solvent was removed under reduced pressure to give the title compound (2) as an oil. The oil was used as is for the next step without further purification.

EXAMPLE 2

Π-Benzyloxymethyl-L-histidine methyl ester (3)

To Nα-Fmoc-Π-benzyloxymethyl-L-histidine methyl ester (2) (how much) in dichloromethane (100 mL) was added Piperidine (2.0 mL, 20 mmol). The mixture was stirred under an atmosphere of nitrogen for 3 hours. The mixture was concentrated under reduced pressure. The residue was diluted with methanol (50 mL) and the pH was adjusted to 7.0 with HCl. Filtration yielded the title compound (3) as an oil. The oil was used as-is for the next step without further purification.

EXAMPLE 3

Π-Benzyloxymethyl-L-histidine methyl ester (4)

To Π-Benzyloxymethyl-L-histidine methyl ester (3) in methanol (200 mL) was added sodium cyanoborohydride (5.65 gm, 90 mmol). The pH of the mixture was adjusted to between 5 and 6 using acetic acid. Boc-aminoacetaldehyde (5.54 gm, 35.0 mmol) in methanol (15 mL) was added and the mixture was stirred under an atmosphere of nitrogen for 1 hour. An additional amount of Boc-aminoacetaldehyde (14.4 gm, 91.3 mmol) in methanol (50 mL) was added with stirring for another 12 hours. The mixture was concentrated under reduced pressure. The residue was diluted with ethyl acetate (500 mL) and washed with aqueous sodium bicarbonate (2×200 mL). The organic phase was dried over magnesium sulfate, filtered, and then concentrated under reduced pressure to give a residue. The oil was further purified by silica gel flash column chromatography using ethyl acetate/methanol/hexanes (5:1:5) as the eluent to give 5.33 g (68%) of the title compound as an oil.

$^1$H NMR (CDCl$_3$) δ 1.43 (s, 9H), 1.718 (6x, 1H, NH), 2.55 (m, 2H), 2.71 (m, 2H), 2.99 (m, 2H), 3.11 (m, 2H), 3.53 (t, 1H), 3.68 (s, 3H), 4.42 (s, 2H), 4.80 (bs, 1H, NH), 5.33 (S, 2H), 6.88 (s, 1H), 7.31 (m, 5H) and 7.48 (s, 1H). MS-FAB in negative mode, (Calc.); Found: (432.5); 431.1.

EXAMPLE 4

Nα-(N-Boc-2-aminoethyl)Π-benzyloxymethyl-L-histidine methyl ester (5)

To Π-Benzyloxymethyl-L-histidine methyl ester (4) (5.33 gm, 12.3 mmol) in DMF (100 mL) and dichloromethane (50 mL) was added N,N-diisopropylethylamine (3.5 mL, 25 mmol) and thymin-1-yl-acetic acid (1.75 gm, 9.5 mmol). After stirring at room temperature for 20 minutes PyBrop (8.85 gm, 19 mmol) was added and the mixture was stirred for an additional 12 hours under an atmosphere of nitrogen. The solvent was removed under reduced pressure and the residue was purified by silica gel flash column chromatography using hexanes/methanol/ethyl acetate (4:1:5) as the eluent to give 1.5 (20%) of the title compound.

Proton NMR was consistent with structure.

EXAMPLE 5

Nα-(N-Boc-2-aminoethyl)Π-benzyloxymethyl-L-histidine (6)

To Nα-(N-Boc-2-aminoethyl)Π-benzyloxymethyl-L-histidine methyl ester compound (5) (1.5 gm, 2.5 mmol) in methanol (100 mL) was added sodium hydroxide (0.8 gm, 20 mmol). The mixture was allowed to stand for 12 hours and the solvent was removed under reduced pressure. The residue was purified by silica gel flash column chromatography using ethyl acetate/methanol (4:1) as the eluent to give 1.1 g (75%) of the title compound.

Proton NMR was consistent with structure. MS-FAB in negative mode, (Calc.); Found: (584.6); 582.6.

EXAMPLE 6

Nα-(N-Boc-2-aminoethyl)Π-benzyloxymethyl-D-histidine (D-6)

Following the procedures illustrated in examples 1–5, and starting with Nα-Fmoc-Π-benzyloxymethyl-D-histidine (Sigma Chemical Company, 9.0 gm, 18.1 mmol) the D isomer was synthesized.

Proton NMR was consistent with structure. MS-FAB in negative mode, (Calc.); Found: (584.6); 582.1.

Various modifications of the invention, in addition to those described herein, will be apparent to those skilled in the art from the foregoing description. Such modifications are intended to fall within the scope of the appended claims.

What is claimed is:

1. A compound of formula:

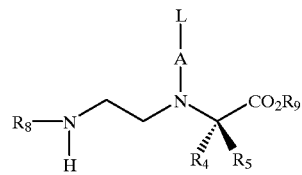

wherein:

$R_8$ is H or an amine protecting group;

$R_9$ is H or alkyl having from 1 to about 12 carbon atoms or alkenyl having from 2 to about 12 carbon atoms;

one of $R_4$ and $R_5$ is H and the other of $R_4$ and $R_5$ is a moiety of formula (II)

(II)

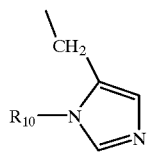

wherein
$R_{10}$ is an amine protecting group
L is selected from the group consisting of hydrogen, hydroxy, $(C_1-C_4)$alkanoyl, naturally occurring nucleobases, non-naturally occurring nucleobases, aromatic moieties, DNA intercalators, nucleobase-binding groups, and heterocyclic moieties, reporter ligands, wherein amino groups are, optionally, protected by amino protecting groups;
A is a group of formula (IIa)–(IId):

(IIa)
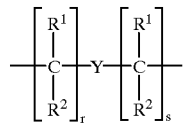

(IIb)
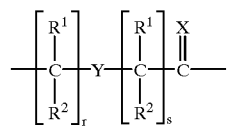

(IIc)
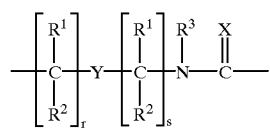

(IId)
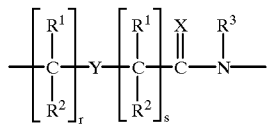

where:
X is O, S, Se, $NR^3$, $CH_2$ or $C(CH_3)_2$;
Y is a single bond, O, S or $NR^4$ where $R^4$ is as described above;
each r and s is zero or an integer from 1 to 5;
each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and
$R^3$ is selected from the group consisting of hydrogen, $(C_1-C_4)$alkyl, hydroxy- or alkoxy- or alkylthio-substituted $(C_1-C_4)$alkyl, hydroxy, alkoxy, alkylthio and amino.

2. The compound of claim 1 wherein $R_8$ is selected from the group consisting of allyloxycarbonyl, benzyloxycarbonyl, t-butyloxycarbonyl, fluorenylmethyloxycarbonyl, isonicotinyloxycarbonyl groups.

3. The compound of claim 1 wherein $R_9$ is alkyl having 1 to about 7 carbon atoms.

4. The compound of claim 1 wherein $R_{10}$ is selected from the group consisting of t-butyloxycarbonyl, t-butyloxymethyl, fluorenylmethyloxycarbonyl, 2,4-dinitrophenyl and isonicotinyloxycarbonyl groups.

5. The compound of claim 1 wherein $R_{10}$ is benzyloxymethyl.

6. The compound of claim 1 wherein L is a nucleobase.

* * * * *